United States Patent
Harvey et al.

(10) Patent No.: US 11,932,724 B1
(45) Date of Patent: Mar. 19, 2024

(54) HIGH DENSITY POLYMERS BASED ON NORBORNADIENE

(71) Applicant: The United States of America, as represented by the Secretary of the Navy, Arlington, VA (US)

(72) Inventors: Benjamin G. Harvey, Ridgecrest, CA (US); Kyle E. Rosenkoetter, Ridgecrest, CA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 54 days.

(21) Appl. No.: 17/220,282

(22) Filed: Apr. 1, 2021

Related U.S. Application Data

(60) Provisional application No. 63/004,307, filed on Apr. 2, 2020.

(51) Int. Cl.
*C08F 36/02* (2006.01)
*C07C 1/20* (2006.01)
*C08G 61/02* (2006.01)

(52) U.S. Cl.
CPC .......... *C08G 61/02* (2013.01); *C07C 1/20* (2013.01); *C08F 36/02* (2013.01); *C08F 2500/07* (2013.01); *C08G 2261/13* (2013.01); *C08G 2261/3325* (2013.01); *C08G 2261/592* (2013.01); *C08G 2261/76* (2013.01)

(58) Field of Classification Search
CPC .......... C08F 36/00; C08F 36/04; C08F 36/22; C08F 2/02; C08F 200/07; C08F 2500/32; C08F 2500/07
See application file for complete search history.

(56) References Cited

U.S. PATENT DOCUMENTS

| | | | | |
|---|---|---|---|---|
| 4,031,150 A | * | 6/1977 | Suld | C07C 2/42 585/362 |
| 4,165,969 A | * | 8/1979 | Hughes | C10L 1/322 44/281 |

FOREIGN PATENT DOCUMENTS

| | | | | |
|---|---|---|---|---|
| JP | 2009-070964 A | * | 4/2009 | H01L 21/312 |
| WO | WO 93/02121 A1 | * | 2/1993 | C08G 61/08 |
| WO | WO 2016/163371 A1 | * | 10/2016 | C08F 232/00 |

OTHER PUBLICATIONS

Rosenkoetter, K.E.; Garrison, M.D.; Quintana, R.L.; Harvey, B.G. ACS Appl. Polym. Mater. 2019, 1, 2627-2637. (Year: 2019).*

(Continued)

*Primary Examiner* — Rip A Lee
(74) *Attorney, Agent, or Firm* — Naval Air Warfare Center Weapons Division; Stuart H. Nissim

(57) ABSTRACT

A novel family of cycloalkanes compounds having one or more allylidene functionalities which can be used to create cross-linked thermosets and thermoplastics having thermal stability. An example heptacyclo [$6.6.0.0^{2,6}.0^{3,13}.0^{4,11}.0^{5,9}.0^{10,14}$] tetradecane (HCTD) complex with terminal allylidene groups at the 7- and 12-positions (HCTD-7,12-diallylidene) was generated from norbornadiene via an efficient six-step synthesis. Thermal polymerization at temperatures ranging from 160 to 240° C. yielded a robust cross-linked material with thermal stability up to 485° C. in air, a glass transition temperature of 377° C., and a char yield (600° C.) of 56% in air. Applications include heat resistant composites utilized in the aerospace, electronic, automotive and textile industries.

18 Claims, 4 Drawing Sheets

(56) References Cited

OTHER PUBLICATIONS

Story, P.R. J. Org. Chem. 1961, 26, 287-290. (Year: 1961).*
Story, P.R.; Fahrenholtz, S.R. J. Org. Chem. 1963, 28, 1716-1717. (Year: 1963).*

* cited by examiner

HIGH DENSITY POLYMERS BASED ON NORBORNADIENE

CROSS-REFERENCE TO RELATED APPLICATIONS

This is a non-provisional application, which claims the benefit of parent application Ser. No. 63/004,307 filed on Apr. 2, 2020, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention generally relates to high density oligomers and polymers from cycloalkanes with allylidene functionalities and their preparation from norbornadiene.

DETAILED DESCRIPTION OF EMBODIMENTS OF THE INVENTION

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are also illustrated schematically in the accompanying drawings and in the appended claims.

The invention generally relates to novel high density cross-linking hydrocarbon networks with densities exceeding 1.2 g/mL would increase the volumetric energy density of the binder by greater than 30%.

A unique thermosetting monomer combining a rigid multicyclic core structure and apical allylidene groups has been prepared from norbornadiene. This monomer thermally cures at modest temperatures to generate a highly cross-linked material with no release of volatiles. DSC, IR, solid state NMR, and inhibitor studies suggest that the allylidene groups primarily cross-link through free radical polymerization of the terminal alkenes. The resulting material exhibits remarkable thermal stability, including a $T_g$ of 377° C., $T_{d5}$ at 485° C., and a char yield of 56% in air at 600° C.

These properties rival those of high temperature polyimides and suggest that this new polymer may have utility for aerospace and defense applications. These monomers are the first of a new class of thermosetting resins with cross-linking exocyclic allylidene groups. The method of the present invention provides an easy pathway for preparing these monomers. In embodiments these compounds can be used in carbon fiber composites. In additional embodiments, the compounds of the present invention can be used in blends with co-monomers.

Figure 2:
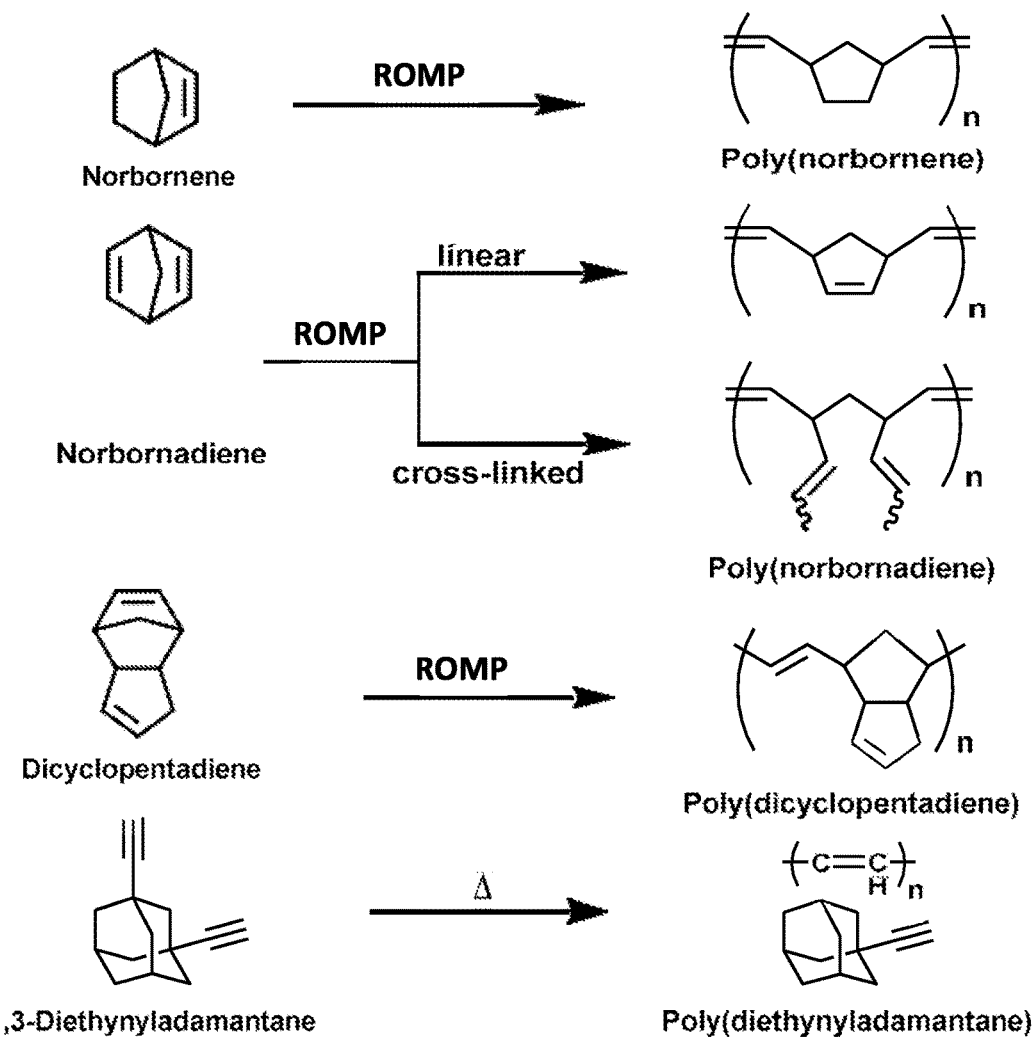
FIG. 2 is an illustration of ring-opening metathesis polymerization (ROMP) of norbornene, norbornadiene, dicyclopentadiene, and thermal polymerization of 1,3-diethynyladamantane according to embodiments of the invention.

The polymerization chemistry of multicyclic compounds such as norbornene, norbornadiene, and dicyclopentadiene (See FIG. 2) has been explored. However, although HCTD complexes have previously been described, their incorporation into thermoplastic or thermosetting resins has not been reported.

Hydroxyl-terminated polybutadiene is used extensively as a binder in propellant formulations and is a significant component of current solid fuel ramjet formulations. The elastomeric properties of HTPB, along with its ability to readily cross-link at low temperature with isocyanate curatives, have contributed to its wide-spread use in propellants. One drawback of HTPB is its relatively modest density of ~0.9 g/mL which can limit the volumetric net heat of combustion of propellant formulations. The development of high density cross-linking hydrocarbon networks with densities exceeding 1.2 g/mL would increase the volumetric energy density of the binder by greater than 30%. Moreover, the incorporation of different functional groups provides an opportunity to eliminate carcinogenic isocyanates from propellant formulations. High density multicyclic hydrocarbons have been extensively studied as liquid fuels for turbine engines and ramjets. Selective functionalization of this class of molecules with flexible cross-linking groups provides a pathway to thermoset materials with similar mechanical properties to HTPB, while exhibiting increased density and enhanced energy output. In addition, through targeted design of the multicyclic hydrocarbons, the rate of pyrolysis and combustion efficiency of the thermoset network can be optimized. The creation of new hydrocarbon binders has the potential to directly increase the range of weapon systems powered by solid fuel ramjets and solid rocket motors.

One embodiment of the method of preparing the compounds of the present invention, comprises:

1. Norbornadiene is functionalized with an alkoxide (—OR3) at the 7-position.
2. A norbornadiene dimer cage structure with alkoxides at the 7- and 12-positions is synthesized.
3. The alkoxides of the cage structure are converted to alcohols.
4. The alcohols are oxidized to ketones.
5. The carbonyl carbons are functionalized with a polymerizable group, preferably a pendent alkene. The resulting cage compounds have tertiary alcohols at the 7- and 12-positions.
6. The alcohols are eliminated via a dehydration reaction to generate alkenes or allowed to react with a selective reducing agent.
7. Functionalized cage structures are polymerized.
8. In embodiments, the polymers can be cross-linked to form thermoset networks.

EXAMPLES

Example 1

HCTD Monomer

Figure 3:
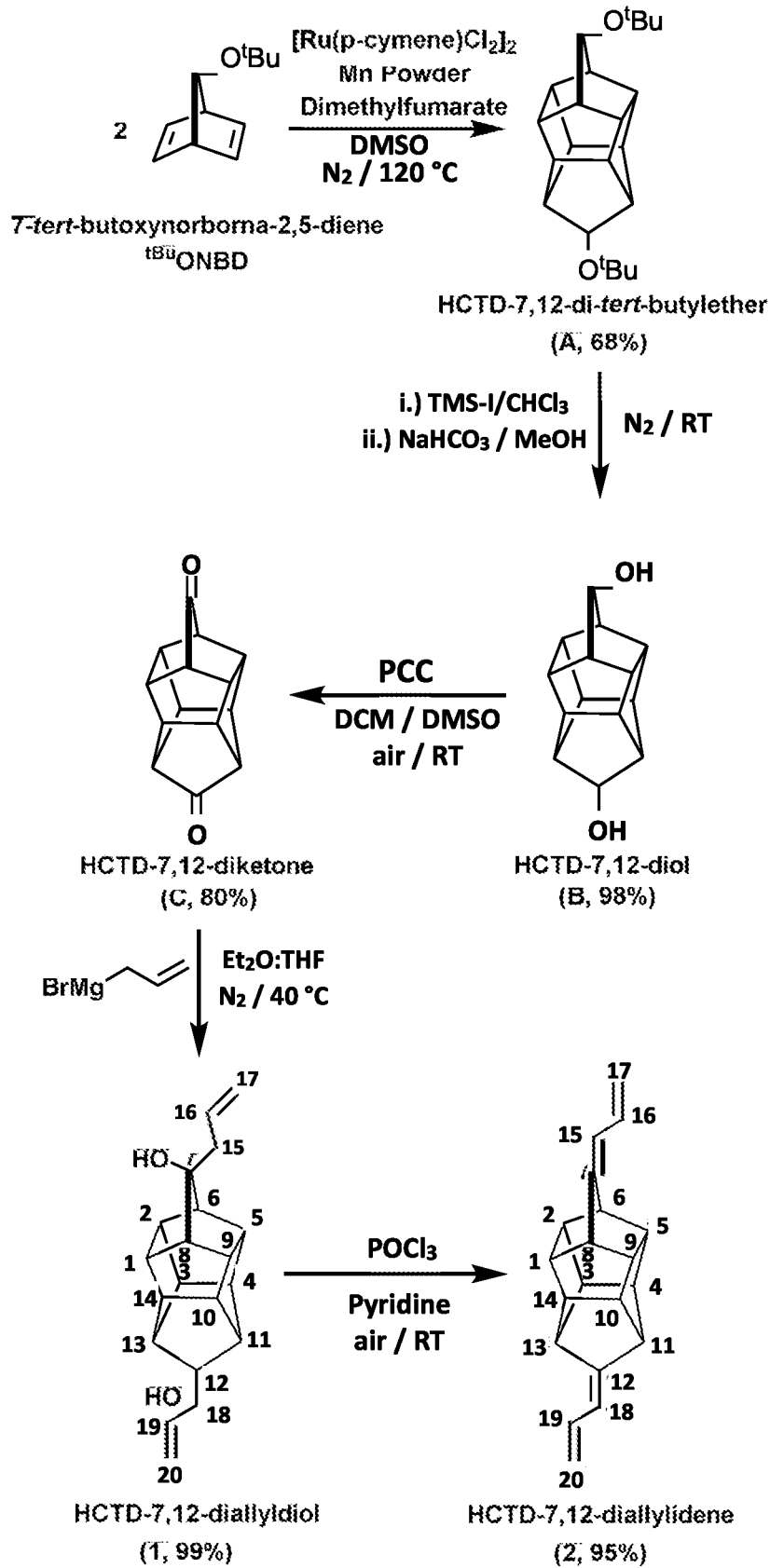
FIG. 3 is an illustration of synthetic pathways utilized in Example 3-7 according to embodiments of the invention.
Figure 4:
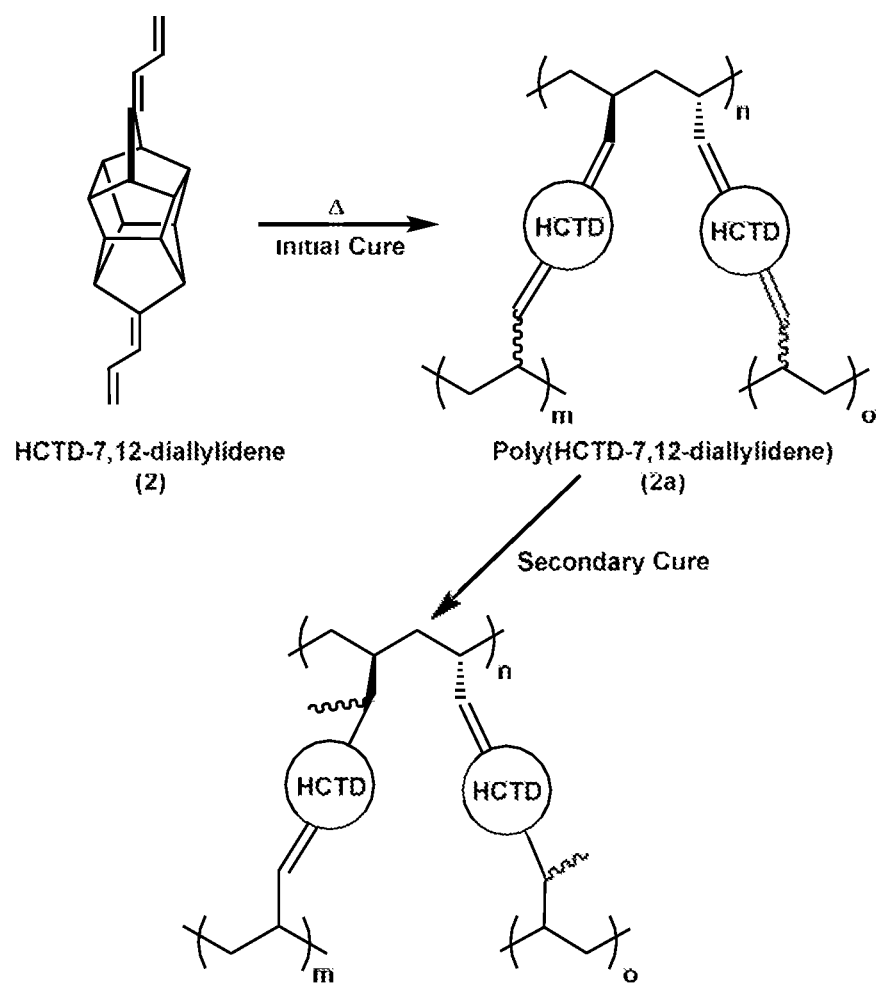
FIG. 4 is an illustration of a possible polymerization mechanism to form poly (HCTD-7,12-diallylidene) according to embodiments of the invention.
Figure 5:
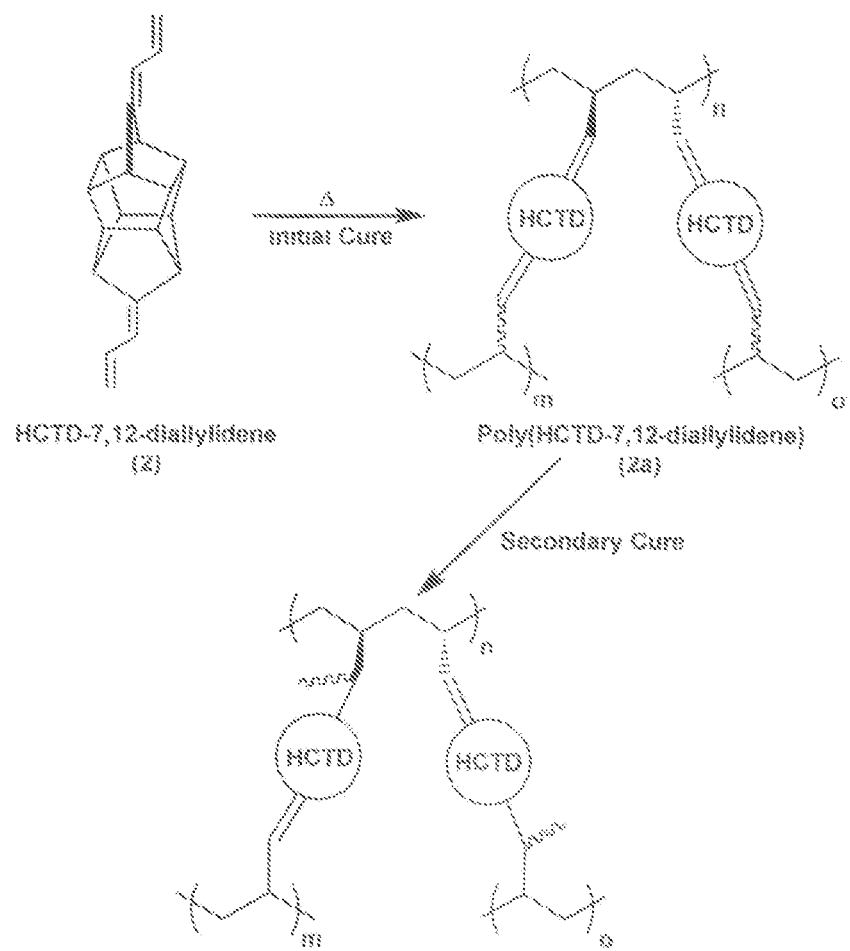

Monomer Synthesis. As illustrated in the example in FIG. 3, HCTD cage complexes with pendent allyl- and allylidene functional groups in the 7- and 12-positions were synthesized through a five-step process starting from 7-tert-butoxynorborna-2,5-diene.

The 7-position of norbornadiene is substituted with —$OR_3$ utilizing a peroxide having the general formula RO—OR or RO—OR', where R=methyl, ethyl, propyl, tert-butyl, isopropyl, for example.

The substituted norbornadiene is converted to a dimer cage compound with transition metal catalyst including, for example, but not limited to, metal carbonyl, ruthenium-based catalysts, or any catalyst capable of performing a [4+4] cycloaddition. In embodiments the catalyst is [Ru(p-cymene)$Cl_2]_2$ The bis(alkoxide) is then reduced to a bis(diol), in the presence of a base, with reagents including $SiR_3$—X, where R is an alkyl group including methyl, ethyl, for example, and X=Cl, Br, or I. In embodiments the base is lutidine. The reaction is then quenched by addition to a basic alcohol solution. In embodiments the basic solution contains an alkali bicarbonate, including $NaHCO_3$ or $KHCO_3$. In embodiments the alcohol is selected from methanol, ethanol, isopropyl alcohol, n-butanol, and tert-butanol).

The bis(diol) is converted to a bis(ketone) by exposure to a strong oxidant. In embodiments the oxidant can be selected from reagents including, but not limited to, chromic acid, sodium dichromate, pyridinium chlorochromate, potassium permanganate, and copper oxide.

The bis(ketone) is allowed to react with an alkylating reagent including, for example, an organolithium, Gilman, organotin, or Grignard reagent. In preferred embodiments, the alkylating reagent is allyl Grignard or allyl lithium.

The bis(alkylated) product, which contains tertiary alcohols at the 7- and 12-positions of the cage, is dehydrated using an acid catalyst. In embodiments, liquid mineral acid catalysts including $H_3PO_4$ or $H_2SO_4$ can be utilized. In other embodiments, organic molecules with carboxylic acids, including oxalic and benzoic acid can be utilized. In still other embodiments, acid catalysts including Amberlyst, p-toluenesulfonic acid, and Nafion can be utilized. In a preferred embodiment, a phosphoryl halide and base is used to dehydrate the molecule. Alternatively, the bis(alkylated) product is reduced without elimination to form an alkene. In embodiments this transformation is conducted by reaction with a silane, including those having the formula $HSiR_3$, where R=methyl, ethyl, hexyl, or phenyl, in the presence of a Lewis acid. In embodiments the Lewis acid is based on Sn (IV). In other embodiments the Lewis acid is selected from $BX_3$, where X=F, Cl, Br, or I. In still other embodiments a Bronsted acid, including trifluoracetic acid can be used as a catalyst.

Example 2

Polymerization

Thermal polymerization was achieved by heating the neat solid monomer to 200° C. under inert conditions for two hours. A sample of HCTD-7,12-diallylidene (Example 7 below) immediately melted and then cured upon placement in a pre-heated oil bath, producing an insoluble, thermoset material (Example 10) in quantitative yield which was isolated as a hard, transparent, pale yellow solid. The density of the polymer (1.18 g/$cm^3$) was measured using a pycnometer, which revealed a similar density to that of the parent hydrocarbon, HCTD-7,12-diallylidene (1.22 g/$cm^3$). The relatively high density of the polymer, as compared to conventional aliphatic hydrocarbon polymers (ρ<1.0 g/$cm^3$), suggested that the HCTD core remained intact during polymerization.[14-16] Similarly, 7-allylidenenorbornane (Example 9 below) was heated at 180° C. in a Teflon sealed Schlenk tube under nitrogen for 16 h. The contents of the flask changed from a clear, colorless liquid to a vibrant orange sticky residue (Example 11 below).

The cage compound prepared in Example 1 can be polymerized by methods including, but not limited to, metathesis polymerization, free radical polymerization, Diels Alder cycloaddition, thermal polymerization, and thiol-ene chemistry.

In embodiments, one or more co-monomers can be used in the polymerization process. In a preferred embodiment, a Ru, Mo, or W-based olefin metathesis is used for the metathesis polymerization reaction.

The polymers can also be cross-linked through methods including thiol-ene chemistry and free radical polymerization. In embodiments, one or more cross-linking agents can be added to the polymers prior to cross-linking.

Figure 1:
FIG. 1 is an illustration of the structure of multicyclic cage compounds according to embodiments of the invention.

Heptacyclo[6.6.0.0$^{2,6}$.0$^{3,13}$.0$^{4,11}$.0$^{5,9}$.0$^{10,14}$]tetradecanes (HCTD) represent a unique class of cage molecules with highly symmetrical structures. Similar to the multicyclic cubanes (four-membered rings) and adamantanes (six-membered rings), HCTD species are a distinct repository of fused five-membered carbocyclic rings with the structures illustrated in FIG. 1.

Previously, the isolation of HCTD species through the [4+4] cycloaddition of norbornadiene was hindered by low yields (2-3%) and the use of stoichiometric amounts of metal carbonyl complexes. Over the last several decades, efforts have been pursued to increase the yield of HCTDs, as well as to functionalize the secondary carbons at the 7- and 12-positions. A high yield synthesis (66%) for the formation of the [4+4] cycloaddition product using a ruthenium based catalyst in DMSO was demonstrated. The same transformation was attempted using THF or DMF and only generated 1-2% yields of HCTD, indicating a solvent effect for the cyclization reaction. Building off this result, Dong and coworkers demonstrated the ability to prepare HCTD complexes with various R-group substituents on the apical 7- and 12-positions (R=alkyl, aryl, ether, etc.).

In general, polymers of these simple unsaturated species exhibit high $T_g$s, good mechanical strength, and high thermal stability, leading to their utility in a variety of aerospace and industrial applications. In contrast, polymers based on the adamantane core have only been sparsely investigated since 1960. A notable adamantane monomer, 1,3-diethynyl-adamantane, undergoes thermal cross-linking through one of the ethynyl groups to form high molecular weight poly(diethynyladamantane)(PDA, FIG. 2). PDA exhibits thermal stability up to 450° C. and a $T_g$>260° C. Polyacetylene has been reported to exhibit thermal stability up to about 410° C. with no observable glass transition temperature. The increased thermal stability of PDA compared to polyacetylene can be directly attributed to the presence of the thermodynamically stable adamantane core. Thermosetting monomers based on multicyclic cage compounds have the potential to generate highly cross-linked networks with outstanding resilience towards heat degradation and chemical attack. These properties are of significant interest for fire-retardant coatings, consumer goods, injection molded parts, as well as military, aerospace, and medical applications.

The rigid, strained, and highly compact scaffold of HCTD complexes offers the opportunity to synthesize a unique class of polymers. The examples herein provide pathways for the synthesis of an HCTD-7,12-diallyldiol species which can then be dehydrated to yield HCTD-7,12-diallylidene. Both HCTD cage complexes were isolated as analytically pure solids (99%) in excellent yields without the use of column chromatography. Upon melting, HCTD-7,12-diallyidene readily cross-linked to form a thermally stable polymer network.

The compounds and reactions reported below show various levels of air- and moisture sensitivity, therefore; all manipulations were carried out using standard Schlenk techniques unless otherwise noted.

NMR spectra were collected on Bruker Avance 300 or 500 MHz spectrometers in $CDCl_3$ or $CD_3OD$. Chemical shifts are reported using the standard δ notation in parts per million. Infrared spectroscopy was performed on a Thermo Nexus spectrometer using an MCTA liquid nitrogen cooled detector. The samples were analyzed using attenuated total reflectance (ATR) with a germanium, single reflection crystal.

X-ray diffraction studies were conducted at low temperature (99 K) on a single crystal mounted on a glass fiber using paratone oil.

Example 3

Synthesis of HCTD-7,12-di-tert-butylether

A 250 mL Schlenk flask was charged with a magnetic stir bar, Ru[(p-cymene)$Cl_2$]2 (1.77 g, 2.90 mmol, 0.05 eq.), manganese powder (0.956 g, 17.4 mmol, 0.30 eq.), and dimethylfurnarate (1.7 g, 10.0 mmol, 0.173 eq.). The contents were put under a positive flow of $N_2$. To the flask was added 7-tert-butoxynorborna-2,5-diene (9.5 g, 57.9 mmol, 1.0 eq.). The contents were then suspended in dry, degassed, DMSO (1 M, 60 mL). The flask was equipped with a reflux condenser with an $N_2$ inlet, and the contents were heated to 120° C. in an oil bath overnight. The contents were then quenched with 100 mL of DI water and transferred to a 500 mL separatory funnel. The organic matter was extracted with $Et_2O$ (5×200 mL), and the organic extracts were combined, dried with magnesium sulfate, filtered through a fritted filter, and the volatiles were removed on a rotary evaporator. The dark brown residue was washed with ice cold acetone to yield a white powder (>99% purity by GC-MS; 6.52 g, 68% yield). The product can be further purified by recrystallization from a concentrated acetone solution at −30° C. Characterization data obtained for the isolated material were consistent with literature precedent.[1] $^1$H-NMR (300 MHz, $CDCl_3$) δ/ppm: 4.28 (br. s, 2H, —C(O$^t$Bu)H), 2.75 (br. s, 4H, —CH), 2.34 (br. s, 6H, —CH), 2.17 (br. s, 2H, —CH), 1.18 (br. s, 18H, —C($CH_3$)$_3$). $^{13}$C {$^1$H}-NMR (75.5 MHz, $CDCl_3$) δ/ppm: 86.0, 72.8, 55.7, 53.2, 51.8, 51.3, 48.9, 48.3, 28.6. IR (neat) $\tilde{v}$/cm$^{-1}$: 2967, 1380, 1196, 1082, 1053. GC-MS (DCM): 15.202 min. (328 m/z=[M], 313 m/z=[M-$CH_3$], 255 m/z=[M-OC($CH_3$)$_3$]).

Example 4

Synthesis of HCTD-7,12-diol

To a 100 mL round bottom flask was added HCTD-7,12-di-tert-butylether (8.86 g, 27.0 mmol, 1.00 eq.), a magnetic stir bar, and chloroform (12 mL). The flask was then capped with a rubber septum and put under a positive nitrogen flow. Iodotrimethylsilane (10.0 mL, 70.3 mmol, 2.60 eq.) was then added via a disposable syringe to afford an immediate color change from a clear pale yellow solution to a red/yellow solution. The mixture was stirred for 10 min at ambient temperature and then poured into a 100 mL beaker containing a slurry of $NaHCO_3$ (10 g) in methanol (200 ml). The resulting mixture was swirled for ten additional min, filtered from the residual solid using a Buchner funnel, and the solid was washed with additional methanol (200 mL). The filtrate volatiles were removed under reduced pressure to yield a yellow solid. The solid was suspended and stirred for one h in 250 mL of an aqueous 10% sodium thiosulfate solution. The suspension was then transferred to a fritted filter, washed with additional aqueous 10% sodium thiosulfate (150 mL), water (100 mL), acetonitrile (100 mL), and lastly hexanes (100 mL). The resulting white solid was collected and dried under vacuum to yield a white solid (5.72 g, 98%). Characterization data obtained for the isolated material were consistent with literature precedent.[4] $^1$H-NMR (300 MHz, $CDCl_3$) δ/ppm: 4.54 (br. s, 2H, —C(OH)H), 2.84 (br. s, 4H, —CH), 2.46 (br. s, 6H, —CH), 2.29 (br. s, 2H, —CH). $^1$H-NMR (300 MHz, MeOD-$d_4$) δ/ppm: 4.44 (br. s, 2H, —C(OH)H), 2.80 (br. s, 4H, —CH), 2.44 (br. s, 4H, —CH), 2.40 (br. s, 2H, —CH), 2.24 (br. s, 2H, —CH). IR (neat) $\tilde{v}$/cm$^{-1}$: 3430, 3261, 2952, 1606, 1289, 1197, 1073, 1042. GC-MS (MeOH): 14.217 min. (216 m/z=[M]).

Example 5

Synthesis of HCTD-7,12-diketone

A 500 mL round bottom flask was charged with PCC (8.7 g, 40.5 mmol, 5.83 eq.) and DCM (200 mL) to give an orange suspension. HCTD-7,12-diol from previous Example 4 (1.50 g, 6.94 mmol, 1.00 eq.) was dissolved in a minimal amount of DMSO (75 mL) and diluted to 100 mL with DCM. This solution was then poured all at once into the PCC suspension to afford an immediate color change to a dark red solution. The reaction mixture was stirred at ambient temperature for three days after which diethyl ether (100 mL) was added to the mixture and the contents stirred for an additional 30 min. The contents were transferred to a 1 L separatory funnel, whereby an additional 100 mL of diethyl ether was added, and the mixture shaken. Upon standing, the DMSO layer (roughly 75 mL) was removed prior to the addition of water. The golden yellow diethyl ether layer was washed with copious amounts of water (500 mL), dried with magnesium sulfate, and the volatiles were then removed under reduced pressure to afford a golden yellow solid. The solid was scraped from the walls of the collection flask, transferred to a glass fritted filter, and washed with hexanes (500 mL) to remove a pale pink impurity. The resulting pale yellow/off-white solid (>97% pure by GC-MS) was collected and dried under reduced pressure (1.15 g, 80% yield). Characterization data obtained for the isolated material were consistent with literature precedent.[29] $^1$H-NMR (300 MHz, $CDCl_3$) δ/ppm: 2.84 (br. s, 8H, —CH), 2.44 (br. s, 4H, —CH). IR (neat) $\tilde{v}$/cm$^{-1}$: 2970, 1770, 1750, 1695, 1150, 897. GC-MS (DCM): 14.251 min. (212 m/z=[M]).

Example 6

Synthesis of HCTD-7,12-diallyldiol

A 200 mL three neck round bottom flask was charged with magnesium metal (986 mg, 41.1 mmol, 40-80 mesh, 5.44 eq.), a catalytic amount of 12, diethyl ether (30 mL), and a magnetic stir bar. The flask was equipped with a reflux condenser, a 100 mL addition funnel, and sealed with a rubber septum. The amber suspension was heated to 40° C. in an oil bath under a nitrogen atmosphere. The amber color began to dissipate after about 10 minutes. To the heated suspension was added neat allyl bromide (3.56 mL, 41.1 mmol, 5.44 eq.) dropwise via addition funnel. The addition funnel was rinsed with additional diethyl ether and drained into the reaction flask (10 mL). The contents were allowed to stir at reflux for 90 min to form a cloudy solution of the Grignard reagent. To the heated suspension was added HCTD-7,12-diketone from Example 5 (1.60 g, 7.55 mmol, 1.00 eq.) as a THF solution (40 mL) dropwise through the addition funnel. The reaction mixture immediately turned clear with the formation of a white precipitate. The reaction mixture was allowed to stir at 40° C. for an additional 20 min and was then removed from heat and cooled to 5° C. in an ice bath. The reaction mixture was then quenched with one mL aliquots of DI $H_2O$ (total of 5 mL) and a saturated aqueous $NH_4Cl$ solution (total of 5 mL). The rubber septum was then removed and more DI $H_2O$ (30 mL) and $NH_4Cl$ solution (20 mL) were added. Diethyl ether (50 mL) was then added to the flask and the mixture was stirred until both layers became transparent. The contents were then transferred to a 500 mL separatory funnel and the organic layer was extracted with diethyl ether (2×100 mL). The organic layer was washed with DI $H_2O$ (3×50 mL), dried with $MgSO_4$, filtered through a Buchner funnel, and the volatiles were removed under reduced pressure to yield a white residue. The residue was suspended in cold hexanes, collected on a glass fritted filter, and dried to afford HCTD-7,12-diallyl-diol as a white solid (2.23 g, 99%). $^1$H-NMR (500 MHz, $CDCl_3$) δ/ppm: 5.96-5.89 (m, 2H, allyl-CH), 5.16-5.13 (m, 4H, allyl —$CH_2$), 2.86 (br. s, 4H, cage —CH), 2.57 (br. s, 4H, cage —$CH_2$), 2.46-2.42 (m, 4H, cage —CH), 2.26 (br. s, 2H, cage —CH), 2.17 (br. s, 2H, cage —CH), 1.79 (br. s, 2H, —OH). $^{13}C\{^1H\}$-NMR (125 MHz, $CDCl_3$) δ/ppm: 134.8 (—C(H)=$CH_2$), 118.5 (—C(H)=$CH_2$), 94.1 ($C_{7,12}$ (OH)-allyl), 57.7, 56.3, 52.7, 52.0, 51.1, 50.4, 41.3. IR (neat) $\tilde{v}/cm^{-1}$: 3351 (—OH), 2933 (—CH), 1639 (allyl, weak), 994 (allyl), 910 (allyl). GC-MS (DCM): 15.825 min. (255 m/z= [M-allyl]. Anal. Calcd for $C_{20}H_{24}O_2$: C, 81.04; H, 8.16. Found: C, 80.82; H, 8.30.

Example 7

Synthesis of HCTD-7,12-diallylidene

A 100 mL round bottom flask was charged with HCTD-7,12-diallyl-diol from Example 6 (1.50 g, 5.07 mmol, 1.00 eq.), pyridine (40 mL), and a magnetic stir bar in air. The flask was capped with a rubber septum and placed in an oil bath. To the solution was added phosphoryl chloride (4.0 mL, 43.0 mmol, 8.48 eq.) via a disposable syringe. The reaction mixture remained a pale yellow/colorless solution. The reaction flask was heated to 75° C. (removed from the oil bath immediately upon reaching 75° C.), and then cooled slowly to ambient temperature. The reaction mixture slowly turned slightly pink in color over time. After stirring at ambient temperature for 90 min, the reaction mixture was quenched slowly with sequential one mL aliquots of DI $H_2O$ (20 mL). An additional 20 mL of DI $H_2O$ was then added, and the contents were transferred to a 500 mL separatory funnel. The organic layer was extracted with diethyl ether (3×100 mL (clear colorless organic layer, light pink aqueous layer), and washed with DI $H_2O$ (3×50 mL). The organic layer was then isolated, dried with $MgSO_4$, filtered using a Buchner funnel, and volatiles were removed using a rotary evaporator to yield a pale yellow solution. Residual pyridine was removed under high vacuum (0.01 mmHg) to give a white solid. The solid was scraped from the sides of the flask, collected in a 20 mL scintillation vial, and further dried under high vacuum (0.01 mmHg) at room temperature to yield HCTD-7,12-diallylidene as a white solid (1.25 g, 95%). X-ray quality crystals were collected by sublimation at 50° C. under static vacuum (0.01 mmHg) for one week. Compound 2 was stable indefinitely in the solid state under ambient conditions. $^1$H-NMR (500 MHz, $CDCl_3$) δ/ppm: 6.50-6.42 (m, 2H, allyl —CH), 5.66-5.64 (m, 2H, allyl —CH), 5.09-5.06 (m, 2H, allyl —$CH_2$), 4.96-4.86 (m, 2H, allyl —$CH_2$), 3.08 (s, 2H, cage-CH), 2.66 (s, 2H, cage —CH), 2.59 (s, 8H, cage —CH). $^{13}C\{^1H\}$-NMR (125 MHz, $CDCl_3$) δ/ppm: 160.8 ($C_{7,12}$=C(H)—), 134.7 (allyl-C(H)—$CH_2$), 114.12 ($C_{15,18}$ or $C_{17,20}$)$_2$, 114.07 ($C_{15,18}$ or $C_{17,20}$), 53.5, 53.1 52.9, 48.4. IR (neat) $\tilde{v}/cm^{-1}$: 2966 (C—H), 1674 (allylidene), 997 (allylidene), 891 (allylidene). GC-MS (DCM): 14.791 min(260 m/z=[M]).

Example 8

Synthesis of 7-allylnorbornan-7-ol

Utilizing the same procedure for isolation of HCTD-7,12-diallyl-diol from Example 6 using: magnesium metal (764 mg, 31.8 mmol, 2.50 eq.), iodine (cat.), allyl bromide (2.75 mL, 31.8 mmol, 2.5 eq.), and norbornan-7-one (1.40 g, 12.7 mmol, 1.0 eq.). A viscous pale yellow oil was collected (crude yield=1.94 g, 99%). The material was trap-to-trap distilled under vacuum (20 mTorr) with an oil bath temperature incrementally increased from 25 to 100° C. to afford a clear, colorless distillate (873 mg, 45%). $^1$H-NMR (300 MHz, $CDCl_3$) δ/ppm: 5.89-5.85 (m, 1H, allyl-CH), 5.13-5.09 (m, 2H, allyl=$CH_2$), 2.38-2.36 (m, 2H, allyl-$CH_2$), 1.95-1.91 (m, 3H, —CH and —OH), 1.69-1.63 (m, 4H, —CH), 1.23-1.20 (m, 4H, —CH). $^{13}C\{^1H\}$-NMR (75.5 MHz, $CDCl_3$) δ/ppm: 135.0 (—C(H)=$CH_2$), 118.2 (—C(H)=$CH_2$), 85.2 (C(OH)-allyl), 42.0 (—$CH_2$ norbornane), 38.1 (—$CH_2$-allyl), 28.7 (—CH norbornane), 27.7 (—$CH_2$ norbornane). IR (neat) $\tilde{v}/cm^{-1}$: 3400 (—OH), 2956 (—CH), 2878 (—CH), 1639 (allyl, weak), 986 (allyl), 911 (allyl, weak). GC-MS (DCM): 8.85 min (151 m/z=[M-H]), 137 m/z=[M-OH], 111 m/z=[M-allyl].

Example 9

Synthesis of 7-allylidenenorbornane

The same procedure described in Example 7 was followed using 7-allylnorbornan-7-ol (220 mg, 1.44 mmol, 1.00 eq.), $POCl_3$ (400 μL, 4.30 mmol, 2.99 eq.), pyridine (10 ml). The ether extraction was washed with copious amounts of DI water (200 ml), 1M aqueous HCl (200 mL), and an additional water aliquot (100 mL). A clear, pale yellow oil was collected (140 mg, 73%). $^1$H-NMR (300 MHz, $CDCl_3$) δ/ppm: 6.48-6.42 (m, 1H, allylidene-CH), 5.74-5.71 (m, 1Hallylidene-CH), 5.10-4.92 (m, 2H, allylidene-$CH_2$), 2.75 (br. s, 1H, —CH norbornane), 2.30 (br. s, 1H, —CH norbornane), 1.59-1.57 (m, 4H, —$CH_2$ norbornane), 1.36-1.33 (m, 4H, —$CH_2$ norbornane). $^{13}C\{^1H\}$-NMR (75.5 MHz, $CDCl_3$) δ/ppm: 154.9 (7-position C=C(H)—), 134.9 (allyl —CH=C(H)$_2$), 114.0 (—C=C(H)—), 113.6 (allyl —C=$CH_2$), 39.9 (—CH norbornane), 34.9 (—CH norbornane), 28.8 (—$CH_2$ norbornane). IR (neat) $\tilde{v}/cm^{-1}$: 2955

(—CH), 2868 (—CH), 1681 (allylidene), 1609 (allylidene), 988 (allylidene), 893 (allylidene). GC-MS (DCM): 7.81 min (134 m/z=[M]).

Example 10

Synthesis of poly(HCTD-7,12-diallylidene)

A 7 mL, three-inch long scintillation vial was charged with HCTD-7,12-diallylidene (30 mg, 0.12 mmol). Nitrogen was flushed over the top of the vial to fill the headspace and the vial was sealed with a Teflon cap. The vial was submerged within a preheated oil bath (200° C.) to cover the glass of the vial. The solid melted within seconds. Five separate vials containing HCTD-7,12-diallylidene were submerged within the oil bath for 15 min, 30 min, 45 min, 60 min, and 22 hrs. All trials resulted in the isolation of a highly cross-linked, insoluble material in quantitative yield. $^{13}C\{^1H\}$-CPMAS NMR (125 MHz) δ/ppm: 159.4, 154.9, 135.1, 115.3, 67.5, 53.5, 49.4, 36.3. IR (neat) $\tilde{v}/cm^{-1}$: 2953 (C—H), 1679, 890.

Example 11

Synthesis of poly(7-allylidenenorbornane)

A 100 mL Schlenk tube was charged with a clear, colorless solution of 7-allylidenenorbornane (90 mg). The flask was purged with $N_2$ and then submerged in a preheated oil bath (180° C.) for 16 h. The flask was removed from heat and allowed to cool to room temperature. The contents in the flask had changed from a clear, colorless liquid to a vibrant orange sticky residue. $^1$H-NMR (500 MHz, CDCl$_3$) δ/ppm: 6.49 (m), 5.76 (m), 5.11-4.93 (m), 2.44 (br. s), 1.62 (br. s), 1.44-1.26 (m), 0.90 (m). IR (neat) $\tilde{v}/cm^{-1}$: 2951 (C—H), 2868, 1684, 734.

Example 12

Polymerization of HCTD-7,12-Diallylidene in the Presence of a Radical Inhibitor

HCTD-7,12-diallylidene (23-25 mg) was measured into a 20-mL scintillation vial and dissolved with 5 mL of dry, inhibitor-free THF. To the solution was added 1 mol % or 5 mol % of BHT from a freshly prepared solution (18-90 µL) using a 100 µL syringe. The vial was mixed thoroughly for five min, and the volatiles were then carefully removed on a rotary evaporator. The resulting solid was further dried under high vacuum (0.01 mmHg) for an additional five min. The solids were then scraped from the walls using a spatula, packed together, and transferred to an aluminum pan which was hermetically sealed for DSC analysis.

Example 13

To evaluate the structures of the thermally cured materials, (Examples 10 and 11) were subjected to FTIR analysis. The IR spectrum of the material from Example 10 illustrated key stretching frequencies at 890, 1674, and 2966 cm$^{-1}$. The spectrum of material from Example 11 demonstrated similar frequencies at 734, 1684, and 2951 cm$^{-1}$.

Example 14

Poly(HCTD-7,12-diallylidene)

The degree of cure for thermoset from Example 10 was investigated with DSC. No melting point was observed, however, a minor exothermic event was evident near 150° C. This feature was consistent with the reaction of a trace of residual alkenes. A second heating cycle revealed no further curing events. To evaluate the thermal stability of the fully cured material it was subjected to thermogravimetric analysis (TGA) at temperatures up to 600° C. in both air and nitrogen atmospheres displaying an onset of decomposition near 450° C. with exceptional char yields of 56% in both air and nitrogen, 5% weight loss ($T_{d5}$) at 488° C., and 20% weight loss ($T_{d20}$) at 550° C. A TGA experiment conducted under isothermal conditions in nitrogen at 400° C. revealed a weight loss of only 5% after two hours. This unusually high thermal stability for a non-aromatic hydrocarbon polymer is consistent with the rigidity of the HCTD core. The thermal stability of poly(HCTD-7,12-diallylidene) exceeds that of the adamantane-based polymer; fully cured poly(1,3-diethynyladamantane) exhibits a $T_{d20}$ at 476° C. in both air and helium. TGA-FTIR verified that thermoset poly(HCTD-7,12-diallylidene) does not begin to degrade and produce any gaseous products until temperatures greater than 450° C. are reached. Above that temperature, pyrolysis products included methane and molecules with intact HCTD cages.

Although embodiments of the invention are described in considerable detail, including references to certain versions thereof, other versions are possible.

Any prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A resin comprising a polymer containing units derived from cycloalkanes having one or more allylidene functionalities.

2. The resin of claim 1 which is thermoplastic.

3. The resin of claim 1 which is a thermoset.

4. The resin of claim 1 wherein said cycloalkanes are derived from norbornadiene.

5. The resin of claim 1 wherein said cycloalkanes are comprised of heptacyclotetradecane-7, 12-diallylidene.

6. A high density hydrocarbon network comprising the resin of claim 1.

7. The high density hydrocarbon network of claim 6 having a density exceeding about 1.2 g/mL.

8. A high density hydrocarbon network comprising a polymer containing units derived from cycloalkanes having one or more allylidene functionalities and having a density exceeding about 1.2 g/mL.

9. A process for the preparation of a cycloalkane having one or more allylidene functionalities, comprising:
functionalizing norbornadiene with an alkoxide (—OR) at the 7-position,
wherein R is methyl, ethyl, propyl, tert-butyl, or isopropyl to form a functionalized norbornadiene;
converting the functionalized norbornadiene to a norbornadiene dimer cage structure with alkoxides at the 7- and 12-positions;
converting the alkoxides of the norbornadiene dimer cage structure to alcohols;
oxidizing the alcohols to ketones;
functionalizing the ketones with an alkylating agent to form tertiary alcohols;
dehydrating the tertiary alcohols to generate the cycloalkane having one or more allylidene functionalities.

10. The process of claim 9 wherein the functionalized norbornadiene is converted to a norbornadiene dimer cage structure with a transition metal catalyst selected from metal carbonyl, ruthenium-based catalysts, or a catalyst capable of performing a [4+4]cycloaddition.

11. The process of claim 9 wherein the alkoxides at the 7- and 12-positions are reduced to alcohols in the presence of a base, and a reagent SiR3-X, where R is an alkyl group and X is Cl, Br, or I.

12. The process of claim 11 wherein a reduction reaction is quenched with a basic alcohol solution containing an alkali bicarbonate, and an alcohol selected from methanol, ethanol, isopropyl alcohol, n-butanol, or tert-butanol.

13. The process of claim 9 wherein the alcohols are oxidized to ketones by exposure to a strong oxidant.

14. The process of claim 13 wherein the strong oxidant is chromic acid, sodium dichromate, pyridinium chlorochromate, potassium permanganate, or copper oxide.

15. The process of claim 9 wherein the alkylating reagent comprises an organolithium, Gilman reagent, organotin, or Grignard reagent.

16. The process of claim 9 wherein dehydrating the tertiary alcohols is performed with a selective reducing agent.

17. The process of claim 9, further comprising polymerizing the cycloalkane having one or more allylidene functionalities.

18. The process of claim 17 further comprising crosslinking resulting polymers.

* * * * *